United States Patent
Dou et al.

(10) Patent No.: US 10,968,424 B2
(45) Date of Patent: Apr. 6, 2021

(54) BACILLUS SUBTILIS STRAIN, CULTURE METHOD AND USE THEREOF

(71) Applicant: SHANDONG BAILONG CHUANGYUAN BIO-TECH CO., LTD, Dezhou (CN)

(72) Inventors: Guangpeng Dou, Dezhou (CN); Xianbao Shao, Dezhou (CN); Qian Du, Dezhou (CN); Zhaobo Gan, Dezhou (CN); Fanghua Li, Dezhou (CN); Mingzhan Zhang, Dezhou (CN); Tengteng Yang, Dezhou (CN); Shuangshuang Liu, Dezhou (CN)

(73) Assignee: SHANDONG BAILONG CHUANGYUAN BIO-TECH CO., LTD, Dezhou (CN)

( * ) Notice: Subject to any disclaimer, the term of this patent is extended or adjusted under 35 U.S.C. 154(b) by 99 days.

(21) Appl. No.: 16/318,358

(22) PCT Filed: Nov. 28, 2017

(86) PCT No.: PCT/CN2017/113344
§ 371 (c)(1),
(2) Date: Jan. 16, 2019

(87) PCT Pub. No.: WO2018/099366
PCT Pub. Date: Jun. 7, 2018

(65) Prior Publication Data
US 2019/0284521 A1    Sep. 19, 2019

(30) Foreign Application Priority Data

Dec. 2, 2016 (CN) .......................... 201611095535.7

(51) Int. Cl.
| C12N 1/20 | (2006.01) |
| C12N 9/90 | (2006.01) |
| C12R 1/125 | (2006.01) |
| C12P 19/24 | (2006.01) |
| C12P 19/02 | (2006.01) |

(52) U.S. Cl.
CPC .............. *C12N 1/20* (2013.01); *C12N 9/90* (2013.01); *C12P 19/02* (2013.01); *C12P 19/24* (2013.01); *C12R 1/125* (2013.01); *C12Y 501/03* (2013.01)

(58) Field of Classification Search
CPC ... C12N 1/20; C12N 9/90; C12P 19/02; C12P 19/24; C12R 1/125; C12Y 501/03
See application file for complete search history.

(56) References Cited

U.S. PATENT DOCUMENTS

2017/0101637 A1    4/2017  Kim et al.

FOREIGN PATENT DOCUMENTS

| CN | 104894047 A | 9/2015 |
| CN | 104962508 A | 10/2015 |
| CN | 105602879 A | 5/2016 |
| CN | 105602925 A | 5/2016 |
| CN | 106164265 A | 11/2016 |
| CN | 106434494 A | 2/2017 |

OTHER PUBLICATIONS

Chen, et al., "High-level intra- and extra-cellular production of D-psicose 3-epimerase via a modified xylose-inducible expression system in *Bacillus subtilis*", J Ind Microbiol Biotechnol, 2016, DOI 10.1007/s10295-016-1819-6, pp. 1-15.

Jia, "Protein Engineering and Food Grade Expression of Clostridium Bolteae D-psicose3-epimerase", CDFD Engineering Technology I., 2014, No. 12, B024-13, pp. 1-93.

International Search Report issued for PCT/CN2017/113344, dated Feb. 12, 2018.

*Primary Examiner* — Blaine Lankford
(74) *Attorney, Agent, or Firm* — James S. Keddie; Bozicevic, Field & Francis LLP

(57) ABSTRACT

A *Bacillus subtilis* strain or a progeny thereof, a method of culturing the same and uses thereof. The invention also relates to a culture and lysate of the *Bacillus subtilis* strain or its progeny, and a method for producing D-psicose epimerase and producing D-psicose using the *Bacillus subtilis* strain or its progeny.

20 Claims, No Drawings

BACILLUS SUBTILIS STRAIN, CULTURE METHOD AND USE THEREOF

CROSS-REFERENCE TO RELATED APPLICATIONS

This application is a § 371 national phase of International Application No. PCT/CN2017/113344, filed on Nov. 28, 2017, which claims the benefit of Chinese Patent Application No. 201611095535.7, filed on Dec. 2, 2016, which applications are incorporated by reference herein.

TECHNICAL FIELD

The present invention relates to the field of microbial technology. In particular, the present invention relates to a *Bacillus subtilis* strain or a progeny thereof, a method of culturing the same and use thereof. The present invention also relates to a culture and a lysate of the *Bacillus subtilis* strain or a progeny thereof. The present invention also relates to a method for producing a D-psicose epimerase using the *Bacillus subtilis* strain or a progeny thereof, and a method for producing a D-psicose using the *Bacillus subtilis* strain or a progeny thereof.

BACKGROUND ART

*Bacillus subtilis* belongs to the genus of *Bacillus*. This bacterium is a gram-positive bacterium, single cell of the bacterium is 0.7-0.8 by 2-3 micrometers in size; spore is 0.6-0.9 by 1.0-1.5 micrometers in size, having an elliptic shape or a columnar shape, and is located at the center of the bacterial cell or slightly off the center. The bacterial cell do not inflate after formation of spore. The surface of the colony of *Bacillus subtilis* is rough and opaque, and is dull white to pale yellow. The bacterium is an aerobic bacterium.

D-psicose is an important rare sugar which is present in a very small amount in sugarcane molasses, dried fruits, sugar products, wheat and Itea plants in nature. Its name is derived from antibiotic psicofuranine, and a small amount of D-psicose can also be isolated from the antibiotic psicofuranine. D-psicose is absorbed into the blood circulation through small intestine in human body and will not be metabolized into energy after absorption in the small intestine, and it has a low fermentability for intestinal microbes. D-psicose has many important physiological functions: neuroprotection, hypoglycemic activity, lipid-lowering activity, removal of active oxygen species, anti-oxidation, inhibition of cancer cell proliferation, function as a low-calorie sweetener, etc.

D-psicose is the C-3 epimer of D-fructose. The early method for D-psicose synthesis was performed through multistage chemical conversions of a common monosaccharide or a non-sugar precursor, but the multiple operations of protection and deprotection resulted in low yields and complicated synthesis processes, so that it has great limitations. At present, D-fructose has been used as a raw material to produce D-psicose through biotransformation. However, the microorganisms reported so far merely produce D-psicose epimerases with poor transformation ability, and the isolation and purification process are difficult.

The Chinese patent document CN105602879A (application number: 201610051547.3) discloses a genetically engineered strain that efficiently secretes D-psicose 3-epimerase and a construction method thereof. In the invention, a recombinant expression plasmid pMA5-RDPE is constructed by using D-psicose 3-epimerase gene rdpe derived from *Ruminococcus* sp. 5_1_39B_FAA, which is then used to transform *Bacillus subtilis*, thereby realizing the constitutive secretion expression of RDPE in *Bacillus subtilis*. By comparing three sugar-inducible promoters, the optimal inducible promoter PxylA is obtained, and the secretion level of RDPE is significantly increased. By knocking out the xylose utilization gene xylAB (xylA and xylB), the xylose metabolism pathway of *Bacillus subtilis* is blocked, the secretion of RDPE was further increased, and the optimal induction concentration of the inducer xylose is reduced from 4.0% to 0.5%. Finally, using the fed-batch method, the engineered strain 1A751SD-XR is evaluated in a 7.5 L fermentor, and the highest level of RDPE secretion is 95 U/mL and 2.6 g/L. However, the enzymatic activity of this enzyme is still low and cannot meet the needs of actual production.

Therefore, searching for a strain capable of producing D-psicose epimerase with high conversion rate is the key for large-scale production of D-psicose.

CONTENTS OF THE INVENTION

In the present invention, unless otherwise specified, scientific and technical terms used herein have the meanings commonly understood by those skilled in the art. Also, the procedures for microbial culture, biochemistry, cell biology, and the like used herein are all conventional procedures widely used in the respective fields. Meanwhile, in order to better understand the present invention, the definitions and explanations of related terms are provided below.

As used herein, the term "medium" is any solid or liquid medium known in the art for supporting the growth of cells, particularly bacteria such as *Bacillus* bacteria, for example *Bacillus subtilis*. In certain preferred embodiments, the medium (e.g., a first medium, a second medium, a solid medium, a seed medium, or a fermentation medium) as described herein is capable of supporting the growth of bacteria (e.g., *Bacillus* bacteria, for example *Bacillus subtilis*). In such embodiments, the medium typically contains a carbon source, a nitrogen source, inorganic salts, and any other nutrients required for maintenance of the bacteria in a viable state.

As used herein, the term "culture" of a bacterial strain refers to a product obtained after culture of the bacterial strain in a medium.

As used herein, the term "lysate" of a bacterial strain refers to a product obtained after disruption of the cell wall and/or cell membrane of the bacterial strain, which contains intracellular materials. The lysate of a bacterial strain can be obtained by various techniques known in the art, such as sonication, homogenization, osmotic shock, freezing and thawing method, enzymatic dissolving method, and the like.

The inventors of the present application have conducted extensive experiments and repeated trials, and have surprisingly found that the activity of a D-psicose epimerase produced by a specifically mutagenized strain of *Bacillus subtilis* is significantly higher than that of wild type strains of *Bacillus subtilis*. Based on this finding, the present inventors developed a new *Bacillus subtilis* strain, a method for culturing the same, and a method for producing D-psicose based on the strain.

Therefore, in one aspect, the present invention provides a *Bacillus subtilis* strain BLCY-005 or a progeny thereof, the strain BLCY-005 was deposited on Oct. 26, 2016 in the China General Microbiological Culture Collection Center, with an accession number of CGMCC No. 13152.

In certain preferred embodiments, the activity of the D-psicose epimerase produced by the strain or a progeny thereof is increased by at least 30%, at least 35%, at least 40%, at least 45%, at least 50%, at least 60%, at least 70%, at least 80%, at least 90%, or at least 100% in comparison with the D-psicose epimerase produced by a wild-type strain. In certain preferred embodiments, the activity of the D-psicose epimerase produced by the strain or a progeny thereof is increased by at least 90%, or at least 100% in comparison with the D-psicose epimerase produced by a wild-type strain.

In another aspect, the invention provides a culture comprising the *Bacillus subtilis* strain or a progeny thereof as described herein.

In certain preferred embodiments, the culture comprises a medium, such as a solid medium or a liquid medium.

In certain preferred embodiments, the activity of the D-psicose epimerase in the culture is increased by at least 30%, at least 35%, at least 40%, at least 45%, at least 50%, at least 60%, at least 70%, at least 80%, at least 90%, or at least 100% in comparison with the D-psicose epimerase produced by a wild-type strain. In certain preferred embodiments, the activity of the D-psicose epimerase in the culture is increased by at least 90%, or at least 100% in comparison with the D-psicose epimerase produced by a wild-type strain.

In the present invention, the culture can be obtained by culturing the strain of the present invention or its progeny in a medium under culture conditions, and a person skilled in the art knows how to select an appropriate medium and culture conditions according to the strain properties.

In certain preferred embodiments, the culture is obtained by culturing the strain of the present invention or a progeny thereof by the method as described above.

In another aspect, the present invention provides a lysate of a strain, the strain is the *Bacillus subtilis* strain or a progeny thereof as described herein.

In certain preferred embodiments, the lysate comprises a D-psicose epimerase.

In certain preferred embodiments, the activity of the D-psicose epimerase in the lysate is increased by at least 30%, at least 35%, at least 40%, at least 45%, at least 50%, at least 60%, at least 70%, at least 80%, at least 90%, or at least 100% in comparison with the D-psicose epimerase produced by a wild-type strain. In certain preferred embodiments, the activity of the D-psicose epimerase in the lysate is increased by at least 90%, or at least 100% in comparison with the D-psicose epimerase produced by a wild-type strain.

In another aspect, the present invention provides a composition, comprising fructose, and at least one component selected from the group consisting of: (1) the strain of the present invention or a progeny thereof; (2) the culture of the present invention; and (3) the lysate of the present invention.

In certain preferred embodiments, the fructose is obtained or provided in form of an aqueous crystalline fructose solution, liquid fructose, glucose-fructose syrup (e.g. high fructose corn syrup), dried fructose, or fructose syrup.

In another aspect, the present invention provides a method for culturing the *Bacillus subtilis* strain or a progeny thereof as described herein, comprising a step of inoculating the strain or a progeny thereof into a medium.

In certain preferred embodiments, the medium is any solid or liquid medium known in the art for supporting the growth of bacteria (particularly *Bacillus* bacteria, such as *Bacillus subtilis*). In general, the medium contains a carbon source, a nitrogen source, an inorganic salt, and any other nutrient required for maintenance of the bacteria in a viable state.

In certain preferred embodiments, the method comprises the following steps:

(1) inoculating the strain or a progeny thereof of the present invention into a solid medium, and performing cultivation;

(2) inoculating the strain in the solid medium into a first medium, and performing cultivation;

(3) optionally, inoculating the strain in the first medium into a second medium, and performing cultivation.

In certain preferred embodiments, in step (1), the cultivation is performed at a temperature of 25-40° C. (e.g., 25-38° C., 28-40° C., 28-38° C., 28-35° C., or 30-38° C.; for example, 35° C.). In certain preferred embodiments, in step (1), the cultivation is performed at a temperature of 30-38° C. In certain preferred embodiments, in step (1), the cultivation is performed at a temperature of 35° C.

In certain preferred embodiments, in step (2), the cultivation is performed at a temperature of 25-40° C. (e.g., 25-38° C., 28-40° C., 28-38° C., 28-35° C., or 30-38° C.; for example, 35° C.). In certain preferred embodiments, in step (2), the cultivation is performed at a temperature of 30-38° C. In certain preferred embodiments, in step (2), the cultivation is performed at a temperature of 35° C.

In certain preferred embodiments, in step (3), the cultivation is performed at a temperature of 25-40° C. (e.g., 25-38° C., 28-40° C., 28-38° C., 28-35° C., or 30-38° C.; for example, 35° C.). In certain preferred embodiments, in step (3), the cultivation is performed at a temperature of 30-38° C. In certain preferred embodiments, in step (3), the cultivation is performed at a temperature of 35° C.

In certain preferred embodiments, the first medium is a seed medium. In certain preferred embodiments, the second medium is a fermentation medium.

In certain preferred embodiments, the method comprises the following steps:

(1) inoculating the strain or a progeny thereof of the present invention into a solid medium and culturing at a temperature of 25-40° C. for 6-12 hours to obtain an activated strain;

(2) inoculating the activated strain obtained in the step (1) into a seed medium and culturing at a temperature of 25-40° C. for 6-12 hours to obtain a seed liquid;

(3) inoculating the seed liquid obtained in the step (2) into a fermentation medium in a volume ratio of 1-10%, and culturing at a temperature of 25-40° C. (e.g., 25-38° C., 28-40° C., 28-38° C., 28-35° C., or 30-38° C.; for example, 35° C.) for 30-48 h to obtain a bacterial fermentation broth.

In certain preferred embodiments, in step (2), the seed medium comprises: 1% peptone, 0.5% yeast extract powder, 1% sodium chloride, 0.01% anhydrous magnesium sulfate, 0.02% potassium dihydrogen phosphate, and the balance of water (all percentages are weight percentages). In certain preferred embodiments, in step (2), the seed medium has a pH of 6.0-7.0.

In certain preferred embodiments, in step (3), the fermentation medium comprises: 3% yeast extract powder, 2% corn steep powder, 1% glucose, 0.01% anhydrous magnesium sulfate, 0.02% diammonium hydrogen phosphate, 0.02% ammonium sulfate, and the balance of water. In certain preferred embodiments, in step (3), the fermentation medium has a pH of 6.0-7.0.

In certain preferred embodiments, in step (1), the solid medium is LB medium.

In another aspect, the present invention provides a method for preparing a D-psicose epimerase, which comprises a step of lysing the *Bacillus subtilis* strain of the present invention or a progeny thereof and isolating the D-psicose epimerase, or a step of isolating the D-psicose epimerase from the culture or lysate of the present invention.

In certain preferred embodiments, the method comprises the following steps: (1) culturing the strain of the invention under a condition that allows the growth of the strain or a progeny thereof to obtain a fermentation broth of the strain; and (2) isolating the D-psicose epimerase from the fermentation broth obtained in step (1).

In certain preferred embodiments, in step (1), the strain is cultured by a method as described herein.

In certain preferred embodiments, in step (2), the D-psicose epimerase is isolated from the fermentation broth by centrifugation, filtration, dialysis, or chromatography. In certain exemplary embodiments, in step (2), the D-psicose epimerase is isolated from the fermentation broth by centrifugation.

In certain preferred embodiments, in step (2), the D-psicose epimerase is isolated from the fermentation broth by the following steps:

(2a) centrifuging the fermentation broth obtained in step (1) to obtain a precipitate;

(2b) thermally denaturing the precipitate obtained in step (2a);

(2c) drying the product of step (2b) (e.g, by vacuum freeze-drying) to obtain the D-psicose epimerase.

In certain preferred embodiments, in step (2b), the precipitate obtained in step (2a) is thermally denatured at a temperature of 50-60° C. In certain preferred embodiments, in step (2b), the precipitate obtained in step (2a) is thermally denatured at a temperature of 50-60° C. for 40-60 min.

In certain preferred embodiments, in step (2c), the product of step (2b) is vacuum freeze-dried. In certain preferred embodiments, in step (2c), the product of step (2b) is vacuum freeze-dried under conditions of −40 to −60° C. and −20 to −60 kpa.

In certain exemplary embodiments, in step (2a), the fermentation broth is centrifuged under conditions of 10000 r/min for 10 min at 4° C.

In certain exemplary embodiments, in step (2), the D-psicose epimerase is isolated from the fermentation broth by the following steps: (i) centrifuging the fermentation broth obtained in step (1), and discarding the resultant supernatant; (ii) washing the product of step (i); (iii) centrifuging the product of step (ii) to obtain a precipitate, which is a crude enzyme preparation; (vi) thermally denaturing the crude enzyme preparation obtained in step (iii) by placing it in a water bath at 50-60° C. for 40-60 min; (v) vacuum freeze-drying the product of step (vi) under conditions of −40 to −60° C. and −20 to −60 kpa.

In certain exemplary embodiments, in step (ii), the strain is washed with 50 mmol/L Tris-HCl buffer (pH 8.0).

In certain preferred embodiments, the method comprises the following step: isolating the D-psicose epimerase from the culture or lysate of the invention. In certain preferred embodiments, the D-psicose epimerase is isolated from the culture or lysate by centrifugation, filtration, dialysis, or chromatography. In certain exemplary embodiments, the D-psicose epimerase is isolated from the culture by centrifugation.

In another aspect, the invention provides a method of preparing a D-psicose, comprising any one of the following steps:

contacting the strain of the invention or a progeny thereof with fructose;

contacting the culture of the invention with fructose;

contacting the lysate of the invention with fructose; and isolating a D-psicose epimerase from the strain of the present invention or a progeny thereof, or the culture or lysate of the present invention, and contacting the D-psicose epimerase with fructose.

In certain preferred embodiments, the fructose is obtained or provided in form of an aqueous crystalline fructose solution, liquid fructose, glucose-fructose syrup (e.g, high fructose corn syrup), dried fructose, or fructose syrup.

In certain preferred embodiments, the method comprises the following steps: (1) isolating a D-psicose epimerase from the strain or a progeny thereof, culture or lysate of the invention; (2) contacting the D-psicose epimerase obtained in step (1) with fructose; (3) optionally recovering D-psicose from the product of step (2).

In certain preferred embodiments, in step (2), the D-psicose epimerase is contacted with fructose under a condition suitable for D-psicose epimerase activity. In certain preferred embodiments, in step (2), the D-psicose epimerase is contacted with fructose under conditions of pH 5.5-6.5.

In another aspect, there is provided a use of the strain of the present invention or a progeny thereof, the culture of the present invention, or the lysate of the present invention in the manufacture of a D-psicose epimerase.

In another aspect, there is provided a use of the strain of the present invention or a progeny thereof, the culture of the present invention, the lysate of the present invention, or the composition of the present invention in the manufacture of D-psicose.

The present invention also includes the following exemplary embodiments:

1. A *Bacillus subtilis* BLCY-005, as deposited at the China General Microbiological Culture Collection Center (address: Institute of Microbiology, Chinese Academy of Sciences, Building 3, #1 West Beichen Road, Chaoyang District, Beijing) on Oct. 26, 2016 under the accession number of CGMCC No. 13152.

2. A culture method for the *Bacillus subtilis* BLCY-005 according to item 1, characterized in comprising the following steps:

(1) inoculating the *Bacillus subtilis* BLCY-005 into a solid medium, activating and culturing at 30-38° C. for 6-12 hours to obtain an activated strain; (2) inoculating the activated strain obtained in step (1) into a seed medium, and culturing at 30-38° C. for 6-12 hours to obtain a seed liquid;

(3) inoculating the seed liquid obtained in step (2) into a fermentation medium at a volume ratio of 1% to 10%, and culturing at 30-38° C. for 30-48 hours to obtain a fermentation broth.

3. The culture method according to item 2, characterized in that the components of the seed medium in the step (2) are as follows in weight percentages:

protein 1%, yeast extract powder 0.5%, sodium chloride 1%, anhydrous magnesium sulfate 0.01%, potassium dihydrogen phosphate 0.02%, balance of water, pH 6.0-7.0;

4. The culture method according to item 2, characterized in that the components of the fermentation medium in the step (3) are as follows in weight percentages:

yeast extract powder 3%, corn steep powder 2%, glucose 1%, anhydrous magnesium sulfate 0.01%, diammonium hydrogen phosphate 0.02%, ammonium sulfate 0.02%, balance of water, pH 6.0-7.0.

5. A use of the *Bacillus subtilis* BLCY-005 according to item 1 in the manufacture of D-psicose epimerase. 6. The use according to item 5, characterized in the steps as follows:

(a) isolating the fermentation broth as above prepared by centrifugation, washing bacterial cells, centrifuging again, and retaining the resultant precipitate as a crude enzyme preparation;

(b) thermally denaturing the crude enzyme preparation prepared in step (a) in a water bath at 50-60° C. for 40-60 minutes, and then drying by a vacuum freeze-drying machine under conditions of −40 to −60° C. and a working pressure of −20 to −60 kpa to obtain a dry powder of D-psicose epimerase.

7. The use according to item 5, characterized in that the bacterial cells are washed in step (a) with a Tris-HCl buffer solution having a pH of 8.0 and a concentration of 50 mmol/L, and then centrifuged, and the precipitate is retained to obtain the crude enzyme preparation.

8. The use according to item 5, characterized in that the centrifugation in steps (a) and (b) is performed at 4° C. and 10000 r/min for 10 min.

9. A use of the D-psicose epimerase as prepared according to item 5 in the manufacture of D-psicose.

BENEFICIAL EFFECTS OF THE INVENTION

Compared with the prior art, the technical solution of the present invention has at least the following beneficial effects:

(1) The D-psicose epimerase produced by the *Bacillus subtilis* strain BLCY-005 of the present invention has a significantly improved enzyme activity. The enzyme activity of the D-psicose epimerase in the culture or lysate of the strain of the present invention can reach 143 U/ml, which is nearly doubled in comparison with the D-psicose epimerase produced by a wild-type strain, so that production cost may be significantly reduced.

(2) The optimum pH for the D-psicose epimerase produced by the *Bacillus subtilis* strain BLCY-005 of the present invention is 5.5 to 6.5, which is advantageous to the control of contamination during production in comparison with the neutral pH optimal for the D-psicose epimerase produced by the wild-type strain.

(3) The D-psicose epimerase produced by the *Bacillus subtilis* strain BLCY-005 of the present invention is an intracellular enzyme, so that the isolation process is simple, and a dry powder of enzyme preparation can be obtained by simple centrifugation, washing, inactivation and drying, which saves production cost and reduces power consumption.

(4) In the present invention, the D-psicose can be prepared by directly contacting D-fructose with the D-psicose epimerase produced by the strain of the present invention. In comparison with the conventional method for preparing D-psicose by contacting D-fructose with a fermentation broth, the present invention tremendously reduces the difficulty and cost of subsequent purification of D-psicose, and the quality of D-psicose can be significantly improved.

The embodiments of the present invention will be described in detail below with reference to the accompanying drawings and examples, but it will be understood by those skilled in the art that the following drawings and examples are only for illustrating the present invention and are not intended to limit the scope of the present invention. Various objects and advantageous aspects of the invention will become apparent to those skilled in the art from the following detailed description of the drawings and preferred embodiments.

Explanation Regarding Deposit of Biological Material

The present invention relates to the following biological materials that have been deposited at the China General Microbiological Culture Collection Center (Building 3, #1 West Beichen Road, Chaoyang District, Beijing):

*Bacillus subtilis* BLCY-005, accession number: CGMCC No. 13152; deposition date: Oct. 26, 2016.

Specific Models for Carrying Out the Invention

The invention will now be described with reference to the following examples which are intended to illustrate but not limit the invention.

Except where noted, the experiments and methods described in the examples are performed essentially according to conventional methods well known in the art and described in various references. The reagents or instruments used without indicating the manufacturers are all conventional products that can be purchased in the market. Those skilled in the art well know that the examples describe the present invention and are not intended to limit the scope of the present invention. All publications and other references mentioned herein are incorporated by reference in their entirety.

EXAMPLE 1

Mutagenesis and Screening of *Bacillus subtilis*

1.1 Enrichment and Culture

The soil near the pilot plant in Bailong Chuangyuan, Dezhou, Shandong Province, was chosen. After the topsoil was removed with a spade, about 10 g of soil was collected from the position 5-15 cm below the ground. After being diluted 10 times with sterile water, the soil was added to LB medium for enrichment and culturing at 30-38° C. for 24 h.

1.2 Purification and Isolation

Streaking method was used, in which 2 ml of the bacterial solution enriched and cultured in step 1.1 was added and diluted in a large test tube containing 5 ml of sterile water, fully shaking for dispersion. One loop of the diluent was picked up by an inoculating loop in a sterile manner, and was streaked parallel 3 to 4 times on one side of a plate medium, to carry out the first steaking; then the culture dish was rotated about 60 degrees, the leftover on the loop was burn down. After cooling, the second steaking was carried out in the same manner as the first steaking; subsequently, the third and the forth steaking were carried out in the same way. After steaking were completed, the dish lid was closed and the dish was inverted. After culturing at 28-38° C. for 24 hours, single colonies were picked and inoculated on 10 slant mediums, which were numbered as 01 to 10.

The slant seeds numbered 01 to 10 were inoculated into shake flask mediums and cultured at 28-38° C. for 24 hours. The enzyme activity of conversion of D-psicose into D-fructose was measured for the shake flask fermentation broths numbered 01 to 10. The shake flask numbered 06 showed the highest enzyme activity of 75 U/ml.

The components of the plate medium were as follows, all by weight percentages:

peptone 1%, yeast extract powder 0.5%, sodium chloride 1%, balance of water, natural pH;

The components of the slant medium were as follows, all by weight percentages:

peptone 1%, yeast extract powder 0.5%, sodium chloride 1%, agar powder 1%, balance of water, natural pH;

The components of the shake flask medium were as follows, all by weight percentages:

yeast extract powder 3%, corn steep powder 2%, glucose 1%, anhydrous magnesium sulfate 0.01%, diammonium hydrogen phosphate 0.02%, ammonium sulfate 0.02%, balance of water, pH 6.0~7.0.

1.3 Mutagenesis and Screening Ultraviolet mutagenesis was performed on the strain numbered 06. The ultraviolet mutagenesis was performed using a 15 W ultraviolet lamp at a distance of 20 cm, and the irradiation time was 120 s. The resulting high-yield strain was further subjected to nitrosoguanidine mutagenesis to finally obtain a strain named BLCY-005 that produced D-psicose epimerase with high conversion rate. The strain was deposited at the China General Microbiological Culture Collection Center on Oct. 26, 2016 (address: Institute of Microbiology, Chinese Academy of Sciences, Building 3, #1 West Beichen Road, Chaoyang District, Beijing) under the accession number of CGMCC No. 13152. Under optimal condition, the enzyme activity of the D-psicose 3-epimerase produced by the strain reached 143 U/ml.

Enzyme activity measurement method: In a reaction system of 1 ml, 800 µl of a reaction substrate solution was added, in which the reaction substrate solution was a solution containing 100 g/L D-fructose dissolved in 50 ml of phosphate buffer (pH 7.0), then added with 200 µl of the fermentation broth, kept at 55° C. for 10 min, then boiled for 10 min to stop the enzyme reaction.

The yield of D-psicose was measured by HPLC, and the enzyme activity was calculated. Enzyme activity unit (U): the amount of enzyme required to catalyze and produce 1 µmol D-psicose per minute.

EXAMPLE 2

The culture method for the *Bacillus subtilis* BLCY-005 described in Example 1 comprised the following steps:

(1) the *Bacillus subtilis* BLCY-005 was inoculated into LB medium and activated at 35° C. for 12 hours to obtain an activated strain;

(2) the activated strain obtained in step (1) was inoculated into a seed medium and cultured at 35° C. for 12 hours to prepare a seed liquid;

the components of the seed medium were as follows, all by weight percentages:

peptone 1%, yeast extract powder 0.5%, sodium chloride 1%, anhydrous magnesium sulfate 0.01%, potassium dihydrogen phosphate 0.02%, balance water, pH 6.8;

(3) the seed liquid obtained in step (2) was inoculated into the fermentation medium at a volume ratio of 5%, and cultured at 35° C. for 48 hours to obtain a bacterial fermentation broth;

the components of the fermentation medium were as follows, all by weight percentages:

yeast extract powder 3%, corn steep powder 2%, glucose 1%, anhydrous magnesium sulfate 0.01%, diammonium hydrogen phosphate 0.02%, ammonium sulfate 0.02%, balance water, pH 6.8.

The dry enzyme preparation was prepared by centrifugation, washing, sterilization and drying. The optimum enzyme activity was 143 U/ml under the optimum pH of 5.5 to 6.5. The enzyme activity was much higher than 75 U/ml of the original strain.

COMPARATIVE EXAMPLE 1

The culture method for the *Bacillus subtilis* BLCY-005 described in Example 1 comprised the following steps:

(1) the *Bacillus subtilis* BLCY-005 was inoculated into LB medium, and cultured at 28° C. for 12 hours to obtain an activated strain;

(2) the activated strain obtained in step (1) was inoculated into a seed medium, and cultured at 28° C. for 12 hours to prepare a seed liquid;

the components of the seed medium were as follows, all by weight percentages:

peptone 1%, yeast extract powder 0.5%, sodium chloride 1%, anhydrous magnesium sulfate 0.01%, potassium dihydrogen phosphate 0.02%, balance water, pH 5.0;

(3) the seed liquid obtained in step (2) was inoculated into a fermentation medium at a volume ratio of 5%, and cultured at 28° C. for 48 h to obtain the bacterial fermentation broth;

the components of the fermentation medium were as follows, all by weight percentages:

yeast extract powder 3%, corn steep powder 2%, glucose 1%, anhydrous magnesium sulfate 0.01%, diammonium hydrogen phosphate 0.02%, ammonium sulfate 0.02%, balance water, pH 5.0.

The dry enzyme preparation obtained after centrifugation, washing, inactivation and drying was assayed for the enzyme activity at optimum pH of 5.5 to 6.5, and the enzyme activity was 107 U/ml.

From the above results, it can be seen that when the culture conditions were not within the scope of the claims of the present invention, the conversion rate of D-psicose was significantly reduced.

Although specific embodiments of the present invention have been described in detail, those skilled in the art will understand that various modifications and changes can be made to the details according to all the teachings that have been disclosed, and these changes are all within the protection scope of the present invention. The protection scope of the invention is given by the appended claims and any equivalents thereof.

The invention claimed is:

1. A *Bacillus subtilis* strain BLCY-005 or a progeny thereof, wherein the strain BLCY-005 was deposited on Oct. 26, 2016 in the China General Microbiological Culture Collection Center, with an accession number of CGMCC No. 13152.

2. A method for culturing the *Bacillus subtilis* strain according to claim 1, comprising a step of inoculating the strain or a progeny thereof into a medium.

3. The method according to claim 2, wherein the method comprises the following steps:
(1) inoculating the strain or a progeny thereof into a solid medium and culturing at a temperature of 25-40° C. for 6-12 hours to obtain an activated strain;
(2) inoculating the activated strain obtained in the step (1) into a seed medium and culturing at a temperature of 25-40° C. for 6-12 hours to obtain a seed liquid;
(3) inoculating the seed liquid obtained in step (2) into a fermentation medium in a volume ratio of 1-10%, and culturing at a temperature of 25-40° C. for 30-48 h to obtain a bacterial fermentation broth.

4. A culture comprising the *Bacillus subtilis* strain or a progeny thereof according to claim 1 and a culture medium.

5. A lysate of a strain, wherein the strain is the *Bacillus subtilis* strain or a progeny thereof according to claim 1.

6. A composition comprising fructose and at least one component selected from the group consisting of: (1) the strain or a progeny thereof according to claim 1; (2) a culture comprising the *Bacillus subtilis* strain or a progeny thereof; and (3) a lysate of the *Bacillus subtilis* strain or a progeny thereof.

7. A method for preparing a D-psicose epimerase, comprising a step of lysing the *Bacillus subtilis* strain or a progeny thereof according to claim 1 and isolating the D-psicose epimerase, or a step of isolating the D-psicose epimerase from a culture comprising the *Bacillus subtilis* strain or a progeny thereof or a lysate of the *Bacillus subtilis* strain or a progeny thereof.

8. A method for preparing a D-psicose, comprising any one of the following steps:
   contacting the strain or a progeny thereof according to claim 1 with fructose;
   contacting a culture comprising the strain or a progeny thereof with fructose;
   contacting a lysate of the strain or a progeny thereof with fructose; and
   isolating a D-psicose epimerase from the strain or a progeny thereof according to claim 1, or a culture comprising the strain or a progeny thereof or a lysate of the strain or a progeny thereof, and contacting the D-psicose epimerase with fructose.

9. The method according to claim 2, wherein the method comprises the following steps:
   (1) inoculating the strain or a progeny thereof into a solid medium, and performing cultivation;
   (2) inoculating the strain in the solid medium into a first medium, and performing cultivation;
   (3) optionally, inoculating the strain in the first medium into a second medium, and performing cultivation.

10. The method according to claim 9, wherein the method is characterized by one or more of the following items:
    (a) the cultivation is performed at a temperature of 25-40° C. in step (1);
    (b) the cultivation is performed at a temperature of 25-40° C. in step (2);
    (c) the cultivation is performed at a temperature of 25-40° C. in step (3);
    (d) the first medium is a seed medium;
    (f) the second medium is a fermentation medium.

11. The method according to claim 3, wherein the method is characterized by one or more of the following items:
    (a) the seed medium comprises: 1% peptone, 0.5% yeast extract powder, 1% sodium chloride, 0.01% anhydrous magnesium sulfate, 0.02% potassium dihydrogen phosphate, and the balance of water (all percentages are weight percentages) in step (2);
    (b) the seed medium has a pH of 6.0-7.0 in step (2);
    (c) the fermentation medium comprises: 3% yeast extract powder, 2% corn steep powder, 1% glucose, 0.01% anhydrous magnesium sulfate, 0.02% diammonium hydrogen phosphate, 0.02% ammonium sulfate, and the balance of water in step (3);
    (d) the fermentation medium has a pH of 6.0-7.0 in step (3);
    (e) the solid medium is LB medium in step (1).

12. The composition according to claim 6, wherein the fructose is obtained or provided in form of an aqueous crystalline fructose solution, liquid fructose, glucose-fructose syrup, dried fructose, or fructose syrup.

13. The method according to claim 7, wherein the method comprises the following steps:
    (1) culturing the strain under a condition that allows the growth of the strain or a progeny thereof to obtain a fermentation broth of the strain; and
    (2) isolating the D-psicose epimerase from the fermentation broth obtained in step (1).

14. The method according to claim 13, wherein the D-psicose epimerase is isolated from the fermentation broth by centrifugation, filtration, dialysis, or chromatography in step (2).

15. The method according to claim 13, wherein the D-psicose epimerase is isolated from the fermentation broth in step (2) by the following steps:
    (2a) centrifuging the fermentation broth obtained in step (1) to obtain a precipitate;
    (2b) thermally denaturing the precipitate obtained in step (2a);
    (2c) drying the product of step (2b) to obtain the D-psicose epimerase.

16. The method according to claim 15, wherein the method is characterized by one or more of the following items:
    (i) the precipitate obtained in step (2a) is thermally denatured at a temperature of 50-60° C. in step (2b);
    (ii) the product of step (2b) is vacuum freeze-dried in step (2c);
    (iii) the fermentation broth is centrifuged under a condition of 10000 r/min for 10 min at 4° C. in step (2a).

17. The method according to claim 8, wherein the fructose is obtained or provided in form of an aqueous crystalline fructose solution, liquid fructose, glucose-fructose syrup, dried fructose, or fructose syrup.

18. The method according to claim 8, wherein the method comprises the following steps:
    (1) isolating a D-psicose epimerase from the strain or a progeny thereof according to claim 1, or a culture comprising the strain or a progeny thereof or a lysate of the strain or a progeny thereof;
    (2) contacting the D-psicose epimerase obtained in step (1) with fructose;
    (3) optionally recovering D-psicose from the product of step (2).

19. The method according to claim 18, wherein the D-psicose epimerase is contacted with fructose under a condition suitable for D-psicose epimerase activity in step (2).

20. The method according to claim 18, wherein the D-psicose epimerase is contacted with fructose under a condition of pH 5.5-6.5 in step (2).

* * * * *